United States Patent [19]
Kreidl et al.

[11] Patent Number: 5,352,790
[45] Date of Patent: Oct. 4, 1994

[54] PROCESS FOR THE PREPARATION OF 1β-ETHYL-1α-(HYDROXYMETHYL)-1,2,3,4,6,7,12,12Bα-OCTAHYDRO-INDOLO[2,3,-A]QUINOLIZINE AND NOVEL INTERMEDIATES

[75] Inventors: Janos Kreidl; Laszlo Czibula; György Visky; Maria F. née Kirjak; Ida D. née Juhasz, all of Budapest; Judit Brill, deceased, late of Budapest, by Jozsef Meszaros, Jr., Krisztina Erdelyi née Meszaros; Katalin Nogradi, Budapest, all of Hungary

[73] Assignee: Richter Gedeon Vegyeszeti Gyar Rt., Budapest, Hungary

[21] Appl. No.: 877,172

[22] PCT Filed: Oct. 30, 1991

[86] PCT No.: PCT/HU91/00046
  § 371 Date: Jun. 25, 1992
  § 102(e) Date: Jun. 25, 1992

[87] PCT Pub. No.: WO92/07851
  PCT Pub. Date: May 14, 1992

[30] Foreign Application Priority Data
  Oct. 31, 1990 [HU] Hungary .............. 6952/90

[51] Int. Cl.⁵ .......................................... C07D 459/00
[52] U.S. Cl. .......................................... 546/70
[58] Field of Search .......................................... 546/70

[56] References Cited

U.S. PATENT DOCUMENTS

| | | | |
|---|---|---|---|
| 4,036,841 | 7/1977 | Szantay et al. | 546/70 |
| 4,044,012 | 8/1977 | Szantay et al. | 546/70 |
| 4,806,545 | 2/1989 | Szantay et al. | 514/285 |

*Primary Examiner*—Johann Richter
*Assistant Examiner*—Catherine Scalzo
*Attorney, Agent, or Firm*—Herbert Dubno; Jonathan Myers

[57] ABSTRACT

The invention relates to a novel process for the preparation of (−) -1β-ethyl-1α-(hydroxymethyl) -1,2,3,4,6,7,12,12bα-octahydro-indolo[2,3-a]quinolizine of the formula (I)

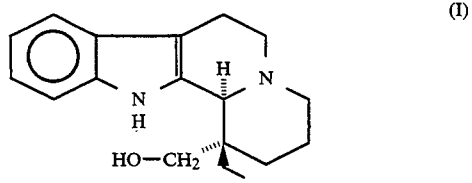

and to novel intermediates obtained in this process. The compound of the formula (I) prepared by the process of the invention possesses a peripheral vasodilator effect.

10 Claims, No Drawings

PROCESS FOR THE PREPARATION OF 1β-ETHYL-1α-(HYDROXYMETHYL)-1,2,3,4,6,7,12,12Bα-OCTAHYDRO-INDOLO[2,3,-A]QUINOLIZINE AND NOVEL INTERMEDIATES

FIELD OF THE INVENTION

The present invention relates to a new process for the preparation of 1β-ethyl-1α-(hydroxymethyl)-1,2,3,4,6,7,12,12bα-octahydro-indolo[2,3-a]quinolizine and novel intermediates. More precisely, the invention relates to a process for the preparation of (—)-1β-ethyl-1α-(hydroxymethyl)-1,2,3,4,6,7,12,12bα-octahydro-indolo[2,3-a]quinolizine of the formula (I)

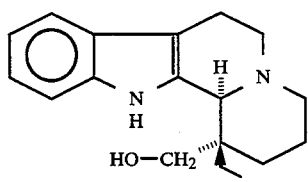

(I)

and to novel intermediates obtained in this process.

BACKGROUND OF THE INVENTION

The compound of the formula (I) having a peripheral vasodilator effect is well known, its preparation and medicinal effect are disclosed in the British patent specification No. 2,174,701.

The racemic 1-ethyl-1-(acyloxymethyl)-1,2,3,4,6,7,12,12bα-octahydro-indolo[2,3-a]quinolizine derivatives used as starting materials in the process described in the British patent specification No. 2,174,701 can be prepared by a method disclosed in the British patent specification No. 1,499,546 by reacting 1-ethyl-2,3,4,6,7,12-hexahydro-indolo[2,3-a]quinolizine of the formula (II)

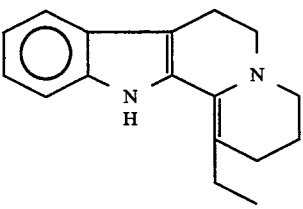

(II)

with formaldehyde used in a high excess. In this case the racemic form of the compound of the formula (I) is obtained. As disclosed in the British patent specification No. 2,174,701, the therapeutically effective β-ethyl-derivative of the formula (I) can be prepared by acylating the above racemic compound, then by resolving the acylated compound thus obtained and then by deacylating the separated β-ethyl form in four reaction steps. The yield of the pharmaceutically ineffective α-ethyl derivative separated in the resolution step is only about 25%, calculated for the starting hexahydro-indolo[2,3-a]quinolizine of the formula (II) when considering the yield data described in Examples 1 and 2 of the British patent specification No. 1,499,546 and Examples 1 and 2 of British patent specification No. 2,174,701.

OBJECT OF THE INVENTION

The object of the invention is to provide a process by which the starting 1-ethyl-hexahydro-indolo[2,3-a]quinolizine of the formula (II) can be converted into the corresponding β-ethyl derivative in a more simple way and with good efficiency and, optionally, the α-ethyl derivative wasted in the previous process can be recycled to the beginning of the synthesis route.

In the course of our experiments for carrying out this process we have surprisingly found that by reacting 1-ethyl-hexahydro-indolo[2,3-a]quinolizine of the formula (II) with about an equimolar amount of formaldehyde or with a polymerized form thereof, racemic 1-(hydroxymethyl)-1,2,3,4,6,7-hexahydro-indolo[2,3-a]quinolizine of the formula (III),

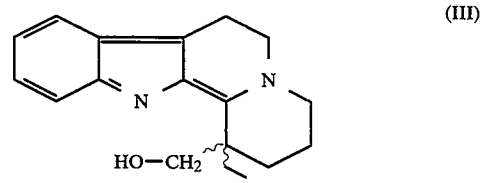

(III)

a new compound, is obtained, from which the target compound can be prepared, in two different ways and in a simple manner, by reducing the novel indolo-quinolizinium salt of the formula (IV),

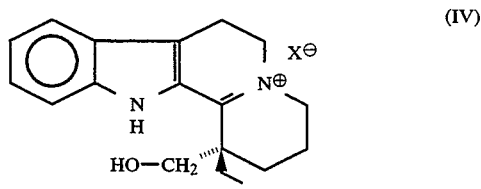

(IV)

wherein X⁻ represents the residue of an optically active acid, thus obtained either a) after a treatment with a resolving agent in an amount less than the equimolar amount, or b) after treatment with a resolving agent in an amount higher than the equimolar amount.

The resolving agent is an optically active acid. Such acids are well known in the art.

SUMMARY OF THE INVENTION

There is provided by this invention a process for the preparation of (—)-1β-ethyl-1α-(hydroxymethyl)-1,2,3,4,6,7,12,12bα-octahydro-indolo[2,3-a]quinolizine of the formula (I). This process is characterized by 1) reacting 1-ethyl-2,3,4,6,7,12-hexahydro-indolo[2,3a]quinolizine of the formula (II) with about an equimolar amount of formaldehyde or with a polymerized form thereof and, after an optional isolation, the novel racemic 1-ethyl-1-(hydroxymethyl)-1,2,3,4,6,7-hexahydro-12H-indolo[2,3-a]quinolizine of the formula (III) obtained:

a) is treated with a resolving agent in an amount less than the equimolar amount and the novel 1β-ethyl-1α-(hydroxymethyl)-1,2,3,4,6,7-hexahydro-12H-indolo[2,3-a]quinolizine-5-ium salt of the formula (IV) obtained is reduced, or b) is treated with a resolving agent in an amount higher than the equimolar amount, then the diastereomer salt pairs of the formulae (IV) and

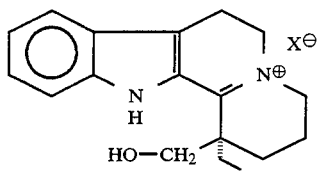
(V)

p1 wherein X⁻ is as defined before, are separated, and the novel 1β-ethyl-1α-(hydroxymethyl)-1,2,3,4,6,7-hexahydro-12H-indolo[2,3-a]quinolizine-5-ium salt of the formula (IV) obtained is reduced to a compound of the formula (I), and, if desired, the novel 1α-ethyl-1β-(hydroxymethyl)-1,2,3,4,6,7-hexahydro-12H-indolo[2,3-a]quinolizine-5-ium salt of the formula (V) obtained is converted into the starting compound of the formula (II) by a treatment with an alkali metal hydroxide, or 2) reacting 1-ethyl-2,3,4,6,7,12-hexahydro-indolo[2,3-a]quinolizine of the formula (II) with about an equimolar amount of formaldehyde or with a polymerized form thereof and with a resolving agent in an amount less than the equimolar amount, then the novel 1β-ethyl-1α-(hydroxymethyl)-1,2,3,4,6,7-hexahydro-12H-indolo[2,3-a]quinolizine-5-ium salt of the formula (IV) is reduced to a compound of the formula (I), or 3) reacting a 1-ethyl-1,2,3,4,6,7-hexahydro-indolo[2,3-a]quinolizine-5-ium salt of the formula (IIa),

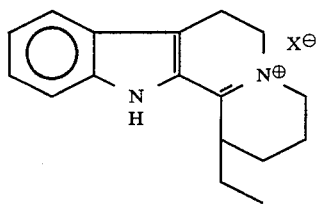
(IIa)

p1 wherein X⁻ is as defined before, with about an equimolar amount of formaldehyde in the presence of a base, and reducing the novel 1β-ethyl-1α-(hydroxymethyl) -1,2,3,4,6,7 -hexahydro-12H-indolo[2,3-a]quinolizine-5-ium salt of the formula (IV) thus obtained, in which X⁻ is as defined above, and optionally liberating the free base of the formula (I).

Further, there is provided a new compound of the formula (III),

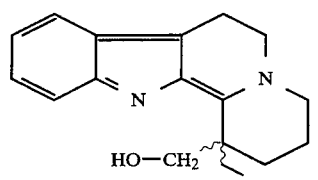
(III)

i.e. 1-ethyl-1-(hydroxymethyl)-1,2,3,4,6,7-hexahydro-12H-indolo[2,3-a]quinolizine.

There is also provided a new compound of the formula (IV),

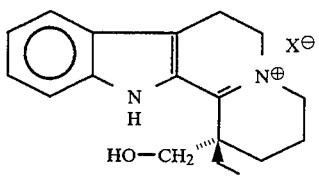
(IV)

wherein X⁻ is as defined before.

There is also provided a new compound of the formula (V),

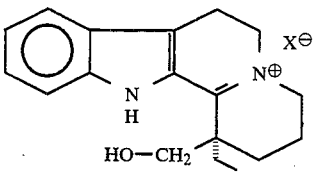
(V)

wherein X⁻ is as defined before.

DETAILED DESCRIPTION OF THE INVENTION

The starting compound of the formula (II) is reacted with about an equimolar amount, preferably 0.9 to 1.1 moles, of formaldehyde or with a polymerized form thereof, e.g. paraformaldehyde, at a temperature near room temperature. The paraformaldehyde is added to a solution of the starting compound of the formula (II) in a protic or dipolar aprotic solvent or a mixture thereof. The novel racemic compound of the formula (III) thus obtained is reacted after isolation, or preferably without isolation, with a resolving agent taken in an amount less than the equimolar amount according to process variant 1a) to obtain a salt of the novel 1βethyl-1α-(hydroxymethyl)-1,2,3,4,6,7-hexahydro-12H-indolo-[2,3-a]quinolizine of the formula (IV) formed with said resolving agent, from which the target compound is obtained by reduction and then optionally after the liberation of the free base.

The above reaction with formaldehyde and the treatment with the resolving agent is carried out at a temperature near room temperature in a dipolar aprotic solvent such as acetone, methyl ethyl ketone, methyl isopropyl ketone, acetonitrile, dimethyl formamide, preferably acetone, or in a protic solvent, such as methanol, ethanol, propanol, isopropanol, preferably isopropanol, or in a mixture of these two solvent types, preferably in acetone containing ethanol or isopropanol.

The resolution of the novel compound of the formula (III) is carried out with an optically active acid, preferably (−)-L-dibenzoyl tartaric acid.

The reduction of the novel compound of the formula (IV) may be carried out in a known manner with a chemical reducing agent, such as sodium borohydride, or by catalytic hydrogenation using as a catalyst preferably palladium on charcoal. When the reduction is carried out with a chemical reducing agent in a water-miscible solvent, such as methanol or ethanol, the target compound of the formula (I) precipitates from the reaction mixture on the addition of water. When the reduction is carried out by catalytic hydrogenation, the target compound is isolated after the liberation of the free base. The deliberation of the free base is carried out in a known manner by the addition of an inorganic base, such as alkali metal hydroxide or ammonium hydroxide.

By performing the above process the compound of the formula (IV) is obtained from the starting compound of the formula (III) with a very good yield nearing to 90%, from which the β-ethyl target compound of the formula (I) is obtained by reduction described above. By this way the starting compound of the formula (II) can be converted into the target compound of the formula (I) with a yield higher than 80% (calculated e.g. on the basis of the yield data of Examples 13 and 8) showing, when compared with the number of the reaction steps and yields of the process according to the British patent specification No. 2,174,701, the exceptional advantages of the process according to the present invention.

According to process variant 1b) the novel racemic compound of the formula (III) obtained in the starting reaction is resolved with a resolving agent used in an amount higher than the equimolar amount. In this case the resolution is carried out in a suitably selected resolving system, such as D-tartaric acid in water, or L-dibenzoyl tartaric acid in an aprotic dipolar solvent, such as acetone, at a temperature near room temperature. When using the later system the expensive L-dibenzoyl tartaric acid may preferably be replaced by a cheaper acid, such as acetic acid, in an equimolar amount of about 0.5.

The starting compound of the formula (II) can be regained from the novel 1α-ethyl-1β-(hydroxymethyl)-1,2,3,4,6,7-hexahydro-12H-indolo[2,3-a]quinolizine-5-ium salt of the formula (V), obtained after separation, by a treatment with a properly selected base, although a therapeutically ineffective stereoisomer of the target compound could be obtained by reducing this salt. The basic treatment can be carried out with an organic base, such as triethyl amine or a dialkyl aniline, or with an inorganic base, such as ammonia or an alkali metal hydroxide, preferably in a heterogeneous phase system comprising an aqueous base and a water-immiscible organic solvent such as chlorinated aliphatic and aromatic hydrocarbons, e.g. dichloromethane, chloroform, dichloroethane and chlorobenzene, or aromatic hydrocarbons e.g. benzene, toluene and xylene; as an aqueous base preferably sodium hydroxide solution may be used. The reaction is preferably performed at a temperature not exceeding 40° C., within 30 to 60 minutes.

If desired, the compound of the formula (II) obtained is isolated in the form of an acid addition salt, such as perchlorate, oxalate or (−)-L-dibenzoyl tartarate, and is re-used as a starting material for the preparation of the therapeutically effective β-ethyl derivative.

The significance of process variant 1b) over the disclosure of the British patent application No. 2,174,701 resides in the fact that the waste, therapeutically ineffective stereoisomer is not produced at all because the corresponding disadvantageous stereoisomer of the formula (V) obtained in the synthesis as a side-product is converted to the starting compound of the formula (II).

Thus, the utilization of the starting hexahydro-indolo-[2,3-a]quinolizine of the formula (II) is about 60 to 70%, calculated for the end-product.

According to process variant 2) the starting compound of the formula (II) is reacted with a nearly equimolar amount of paraformaldehyde in a suitably selected solvent or solvent mixture in the presence of a resolving agent used in less than the equimolar amount calculated for the amount of the starting compound of the formula (II), preferably (−)-L-dibenzoyl tartaric acid, whereafter the compound of the formula (IV) crystallizes from the reaction mixture in one reaction step within a reaction time of several hours with a very good yield of almost 80%, in an optical purity of nearly 100%.

According to process variant 3) one may also proceed by reacting a salt of the starting compound of the formula (II) prepared with an optically active acid, preferably (1-ethyl -1,2,3,4,6,7-hexahydro-12H-indolo[2,3-a]quinolizine-5ium)$_2$ (−) -L-dibenzoyl tartarate, i.e. a compound of the formula (IIa), in a suitably selected solvent or solvent mixture, with a nearly equimolar amount of formaldehyde in the presence of 0.01 to 0.10 equimolar amount of a suitably selected base, such as the starting compound of the formula (II) itself or triethyl amine, preferably the compound of the formula (II), in order to obtain the compound of the formula (IV) in a crystalline form, after stirring the reaction mixture for several hours, with a yield and purity as defined above.

According to this process variant the resolving agent is introduced into the reaction in the form of a salt of the starting compound of the formula (II).

The solvents or solvent mixtures used in process variants 2) and 3) may be the same as defined in process variant 1).

The treatment with the resolving agent as described in process variants 1a), 2) and 3) leads to an asymmetric transformation based on the following: when the compound of the formula (II) is reacted with an equimolar amount of formaldehyde, a "racemic adduct" of the formula (III) is formed. The racemic adduct of the formula (III) is in a dynamic equilibrium with the compound of the formula (II). If less than the equimolar amount of a resolving agent is added to this equilibrium mixture, in a preferred case, one of the diastereomer salts of the racemic adduct of the formula (III) crystallizes out and the other diastereomer salt remaining in the solution becomes racemic through the above described dynamic equilibrium process. This equilibrium exists only in base form and therefore a slight excess of the base is necessary in relation to the resolving acid used.

Summing up the advantages of the process variants 1), 2) and 3) according to the present invention as compared to the process disclosed in the British patent specification No. 2,174,701, it can be stated that the target compound can be prepared in two reaction steps instead of four, and with significantly better yields. If process variant 1b) is carried out, the therapeutically effective β-ethyl compound is obtained with very good yields and also the therapeutically ineffective antipode, which went waste before, can be utilized.

The starting compounds of the formulae (II) and (IIa) are known from the reference Wenkert, E. et al: J. Am. Chem. Soc., 87. 1580 (1965).

The invention is elucidated in more detail by the following non-limiting examples.

EXAMPLE 1

(±) -1-Ethyl-1-(hydroxymethyl) -1,2,3,4,6,7-hexahydro-indolo[2,3-a]quinolizine (III)

37.8 g (0.15 moles) of 1-ethyl-2,3,4,6,7,12-hexahydro-indolo[2,3-a]quinolizine are dissolved in 100 ml of acetone, 5 g of paraformaldehyde are added thereto and the mixture is stirred at room temperature for an hour and a half. Then 30 ml of distilled water are added to the mixture within 15 minutes and the stirring is continued for another hour at 0° C. The precipitated title compound obtained in the form of orange-colored crystals is filtered off and washed in two portions under altogether 20 ml of acetone, at 0° C. Weight: 34.13 g (80.7%), melting point: 111°–113° C.

EXAMPLE 2 a)

(−)-1α-Ethyl-1β-(hydroxymethyl)-1,2,3,4,6,7-hexahydro-12H-indolo[2,3-a]quinolizine-5-ium-(+)-D-tartarate (V)

8.6 g (0.0573 moles) of (+)-D-tartaric acid are dissolved in 160 ml of distilled water and 16.1 g (0.057 moles) of (+) -1-ethyl-1-(hydroxymethyl) -1,2,3,4,6,7-hexahydro-indolo-[2,3-a]quinolizine as prepared in Example 1 are added thereto. The mixture is stirred at room temperature for 10 minutes to obtain a homogeneous solution. This solution is filtered through Celite, if necessary, and allowed to stand for 2 hours. The precipitated crystalline title product is filtered off and washed in two portions, under altogether with 10 ml of acetone weight: 10.2 g, melting point: 103°–105° C., yield: 82.7 %. $[\alpha]^{20}_D$: −81.7° (c=1, methanol).

b)

(+)-1β-Ethyl-1α-(hydroxymethyl)-1,2,3,4,6,7-hexahydro-12H-indolo [2,3-a]quinolizine-5-ium-(+)-D-tartarate (IV)

The aqueous mother liquor obtained as described in point a) above is cooled to 10° C. and allowed to stand for 24 hours. The precipitated compound obtained in the form of crystals is filtered off and washed in two portions under altogether 10 ml of acetone. Weight: 7.2 g, melting point: 136°–139° C., yield: 58.4%, $[\alpha]^{20}_D$: +117° (c=1, methanol).

EXAMPLE 3

(−)-[1β-Ethyl-1α-(hydroxymethyl)-1,2,3,4,6,7-hexahydro-indolo[2,3-a]quinolizine-5-ium]$_2$ (−) -L-dibenzoyl tartarate (IV)

14.1 g (0.05 moles) of (±)-1-ethyl-1-(hydroxymethyl)-1,2,3,4,6,7-hexahydro-indolo[2,3-a]quinolizine as prepared in Example 1 are suspended in 50 ml of acetone. Then a solution of 2 g of acetic acid and 8.5 g (0.0226 moles) of (−)-L-dibenzoyl tartaric acid monohydrate in 30 ml of methanol are added thereto under stirring. The mixture is stirred for 3 hours and filtered off at 20° C., then it is washed under acetone. The title compound is obtained in the form of crystals. Weight: 10 g, melting point: 172°–174° C., $[\alpha]^{20}_D$: −83.2° (c=1, DMF), base content: 59.3% by titrating with HClO$_4$. The yield is 84.1%, calculated for the base content.

EXAMPLE 4

(−)-[1β-Ethyl-1α-(hydroxymethyl)-1,2,3,4,6,7-hexahydro-indolo[2,3-a]quinolizine-5-ium]$_2$ (−) L-dibenzoyl tartarate (IV)

37.8 g (0.15 moles) of 1-ethyl-2,3,4,6,7,12-hexahydro-indolo[2,3-a]quinolizine are dissolved in 100 ml of acetone, 5.2 g of paraformaldehyde are added to the solution and the mixture is stirred for an hour and a half at room temperature. Thereafter 50 ml of acetone are added to the mixture, then a solution of 6 g of acetic acid and 28 g (0.0745 moles) of (−)-L-dibenzoyl tartaric acid monohydrate in 100 ml of methanol is added. The resulting mixture is stirred for 3 hours and the precipitated crystalline title product is filtered off at 20° C. and washed under acetone. Weight: 28 g, melting point: 171°–173° C. [60 ]$^{20}_D$: −82.7° (c=1, DMF), base content: 59.2% by titrating with HClO$_4$. The yield is 78.37%, calculated for the base content.

EXAMPLE 5

1-Ethyl-1,2,3,4,6,7-hexahydro-12H-indolo[2,3-a]quinolizine-5-ium perchlorate (II, salt)

21.6 g of (−)-1α-ethyl-1β-(hydroxymethyl)-1,2,3,4,6,7-hexahydro-12H-indolo[2,3-a]quinolizine-5-ium (+)-D-tartarate as prepared in Example 2a), are suspended in a mixture of 100 ml of water and 100 ml of dichloromethane. 12 ml of concentrated aqueous ammonia are added to the mixture under vigorous stirring and the stirring is continued for 15 minutes. Then 10 ml of a 25% aqueous solution of sodium hydroxide are added and the vigorous stirring is continued for another 15 minutes. The organic phase is separated and the aqueous phase is extracted with 30 ml of dichloromethane. The combined organic phases are dried over magnesium sulphate, filtered off from the drying agent and evaporated. The residue is dissolved in 40 ml of methanol and made acidic to pH 1–2 with a 60% aqueous perchloric acid solution. The precipitated title compound obtained in the form of crystals is filtered off at 0° C. and washed in two portions with altogether 10 ml of cold methanol. Weight: 14.95 g (85%). Melting point: 178° t–180° C.

EXAMPLE 6

[1-Ethyl-1,2,3,4,6,7-hexahydro-12H-indolo[2,3-a]quinolizine-5-ium]$_2$ (−)-L-dibenzoyl tartarate (II, salt)

One proceeds as described in Example 5 with the difference that the solvent-free residue is dissolved in 60 ml of acetone, 9.45 g of (−)-L-dibenzoyl tartaric acid monohydrate are added to the solution and the latter is stirred for 15 minutes under reflux. The title compound obtained in the form of crystals is filtered off at 10° C. and washed in two portions with altogether 10 ml of acetone. Weight: 17.3 g (80%), melting point: 128°–132° C.

EXAMPLE 7

1-Ethyl-1,2,3,4,6,7-hexahydro-12H-indolo[2,3-a]quinolizine-5-ium perchlorate (II, salt)

The mother liquor, containing acetone and methanol, obtained in Example 11 is evaporated in vacuo. 70 ml of dichloromethane and 100 ml of water, further 10 ml of concentrated aqueous ammonia and 8 ml of 25% aqueous sodium hydroxide solution are added thereto under stirring. After stirring for half an hour the organic phase is separated and the aqueous phase is extracted in two portions with altogether 30 ml of dichloromethane. The combined extracts are evaporated, 20 ml of methanol are added to the residue and the solution obtained is acidified to pH 1–2 by adding a 60% aqueous perchloric acid solution. The precipitated title product is filtered off at 0° C. and washed in two portions under altogether 10 ml of cold methanol. Weight: 12.33 g (87%), melting point: 178°–180° C.

From the salt obtained the corresponding free base, i.e. 1-ethyl-2,3,4,6,7,12-hexahydro-indolo[2,3-a]quinolizine, in the form of a solution, in an organic solvent can easily be prepared by phase distribution between a water-immiscible organic solvent, such as dichloromethane or chloroform, and water by the aid of a strong base.

The method described in this example is also suitable for processing the mother liquors obtained in Examples 2, 3, 4, 10 and 12.

EXAMPLE 8

(−)-1β-Ethyl-1α-(hydroxymethyl)-1,2,3,4,6,7,12,12α-octahydro-indolo[2,3-a]quinolizine (I)

47.63 g of (−)-[1β-Ethyl-1α-(hydroxymethyl)-1,2,3,4,6,7-hexahydro-12H-indolo[2,3-a]quinolizine-5-ium]2-(−)-L-dibenzoyl tartarate as prepared in Example 13, having a base content of 59.2%, are suspended in 800 ml of methanol. Then 6.5 g of sodium borohydride are added under stirring in small portions to the suspension until it becomes colorless. The mixture is concentrated into one the third of its original volume in vacuo and 800 ml of water is added thereto. The precipitated white substance is filtered off, washed neutral with water and dried in a vacuum exsiccator. Weight: 27.8 (98%), melting point: 228°–230° C., $[\alpha]^{20}_D$: 108.7° (c=1, DMF).

EXAMPLE 9

(−)-1β-Ethyl-1α-(hydroxymethyl)-1,2,3,4,6,7,12,12bα-octahydro-indolo [2,3-a]quinolizine (I)

4.3 g of (+)-1β-ethyl-1α-(hydroxymethyl)-1,2,3,4,6,7-hexahydro -12H-indolo[2,3-a]quinolizine-5-ium-(+)-D-tartarate as prepared in Example 2b) are suspended in 70 ml of methanol. A total amount of 0.7 g of sodium borohydride are added to the suspension under stirring in small portions at a temperature of 20° C. until the solution becomes colorless. Then 300 ml of water are added to the mixture, the precipitated substance is filtered off and washed neutral with water. Weight: 2.74 g (97%), melting point: 228°–230° C. $[\alpha]^{20}_D$: 108.7 (c=1, DMF).

EXAMPLE 10

(−)-1β-Ethyl-1α-(hydroxymethyl)-1,2,3,4,6,7,12,12bα-octahydro -indolo[2,3-a]quinolizine (I)

10 g of (−)-[1β-Ethyl-1α-(hydroxymethyl)-1,2,3,4,6,7--hexahydro-12H-indolo[2,3-a]quinolizine-5-ium]2-(−)-L-dibenzoil tartarate (base content: 59.3%) are suspended in a mixture of 40 ml of dimethyl formamide and 40 ml of methanol, 1 ml of glacial acetic acid and 0.5 g of a 10% palladium on charcoal are added thereto and the mixture is hydrogenated with elementary hydrogen until hydrogen uptake ceases. The catalyst is filtered out and the filtrate is washed twice with altogether 10 ml of methanol. The methanol is removed from the filtrate by atmospheric distillation and the residue is poured slowly into a mixture of 3 ml of concentrated aqueous ammonia and 120 ml of water under vigorous stirring. The precipitated substance weighing 5.75 g (97%) is filtered off and washed neutral with water. The product obtained is crystallized from dimethyl formamide. Its melting point is 228°–230° C., $[\alpha]^{20}_D$: −108.4° (c=1, DMF).

EXAMPLE 11

(−)-[1β-Ethyl-1α-(hydroxymethyl)-1,2,3,4,6,7-hexahydro-12H-indolo[2,3-a]quinolizine-5-ium]2-(−)-L-dibenzoyl tartarate (IV)

14.1 g (0.5 moles) of (±)-1-ethyl-1-(hydroxymethyl)-1,2,3,4,6,7-hexahydro-indolo[2,3-a]quinolizine as prepared in Example 1 are suspended in 50 ml of acetone and a solution of 8.5 g (0.0226 moles) of (−)-L-dibenzoyl tartaric acid monohydrate in 20 ml of methanol is added thereto under stirring. The mixture is stirred at room temperature for 10 hours, filtered off at 20° C., the precipitated title compound obtained in the form of crystals is washed in two portions under altogether 20 ml of a 5:2 mixture of acetone and methanol and dried. Weight: 18.7 g, melting point: 170°–172° C., $[\alpha]^{20}_D$: −60.4° (c=1, DMF). The base content is 59.2% by titrating with HClO4. The yield is 78.5%, calculated for the base content.

The mother liquor can be processed as disclosed in Example 7.

EXAMPLE 12

(−)-[1β-Ethyl-1α-(hydroxymethyl)-1,2,3,4,6,7-hexahydro-12H-indolo[2,3-a]quinolizine-5-ium]2(−)-L-dibenzoyl tartarate (IV)

37.8 g (0.15 moles) of 1-ethyl-2,3,4,6,7,12-hexahydro-indolo[2,3-a]quinolizine are dissolved in 100 ml of acetone, 5.2 g (0.173 moles) of paraformaldehyde are added thereto and the mixture is stirred at room temperature for an hour and half. Then 50 ml of acetone and a solution of 26 g (0,069 moles) of (−)-L-dibenzoyl tartarate acid monohydrate in 60 ml of methanol is added to the solution. Thereafter the mixture is stirred for 10 hours and the title product obtained in the form of crystals are filtered off at 20° C. and washed in two portions under altogether 60 ml of a 5:2 mixture of acetone and methanol and dried. Weight: 52.5 g, melting point: 170°–172° C. $[\alpha]^{20}_D$: −79.7° (c=1, DMF). The base content is 58 % by titrating with HClO4. The yield is 73%, calculated for the base content.

EXAMPLE 13

(−)-[1β-Ethyl-1α-(hydroxymethyl)-1,2,3,4,6,7-hexahydro-12H-indolo[2,3-a]quinolizine-5-ium]2-(−)-L-dibenzoyl tartarate (IV)

37.8 g (0.15 moles) of 1-ethyl-2,3,4,6,7,12-hexahydro-indolo[2,3-a]quinolizine are reacted with 5.4 g (0.18 moles) of paraformaldehyde in 100 ml of acetone at 20° C. for one hour, then a solution of 26 g (0,069 moles) of (−)-L-dibenzoyl tartaric acid monohydrate in 100 ml of ethanol are added to the mixture. It is stirred for 10 hours at 20° C. The precipitated title product is filtered off and washed in two portions under altogether 50 ml of ethanol. Weight: 61 g, melting point: 170°–172° C., $[\alpha]^{20}_D$: −74.1° (c=1, DMF). The base content is 57.6% and the yield is 89%, calculated for the base content.

EXAMPLE 14

(−)-[1β-Ethyl-1α-(hydroxymethyl)-1,2,3,4,6,7-hexahydro-12H-indolo[2,3-a]quinolizine-5-ium]2(−)-L-dibenzoyl tartarate (IV)

The procedure described in Example 12 is followed except that the same amounts of the starting 1-ethyl-2,3,4,6,7,12-hexahydro-indolo[2,3-a]quinolizine, paraformaldehyde and the (−)-L-dibenzoyl tartaric acid are simultaneously added to 150 ml of acetonitrile and the mixture obtained is stirred at 20° C. for 24 hours. After following the procedure as described in Example 13 the title compound is obtained in an amount of 54.8 g. Yield: 80%.

Example 15

(−)-[1β-Ethyl-1α-(hydroxymethyl)-1,2,3,4,6,7-hexahydro-12H-indolo[2,3-a]quinolizine-5-ium]2(−)-L-dibenzoyl tartarate (IV)

17.3 g of (1-ethyl-1,2,3,4,6,7-hexahydro-12H-indolo[2,3a]quinolizine-5-ium)2 (−)-L-dibenzoyl tartarate and 1.35 g of paraformaldehyde are suspended in a mixture of 160 ml of acetonitrile and 10 ml of methanol, 0.4 g of triethylamine are added thereto and the mixture is stirred at room temperature for 24 hours. From the reaction mixture the title product is filtered off at 0° C. in the form of crystals, washed in two portions with altogether 10 ml of methanol and dried. Weight: 14.4 g, yield: 78%.

What we claim is:

1. A process for the preparation of an optically active compound of the Formula (I)

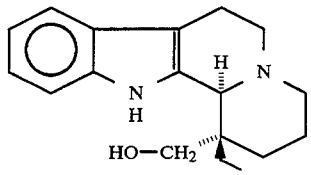

which comprises the steps of:
(a) treating a compound of the Formula (II)

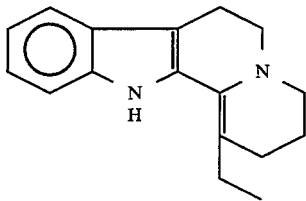

with about an equimolar amount of formaldehyde or with a polymerized form thereof at a temperature near room temperature, to yield a racemic compound of the Formula (III)

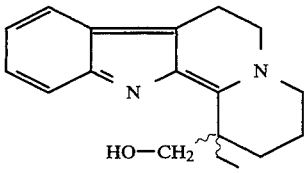

which is in dynamic equilibrium with the compound of the Formula (II) and which may optionally be isolated;
(b) asymmetrically transforming the racemic compound of the Formula (III) with (−)-L-dibenzoyltartaric acid monohydrate, which is a resolving agent, wherein the compound of the Formula (III) is employed slightly in excess of the equivalent amount of the resolving compound to obtain a crystalline optically active salt of the Formula (IV)

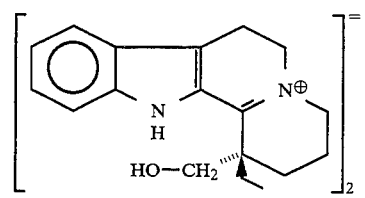

having a desired optical activity and an optically active salt of the Formula (V)

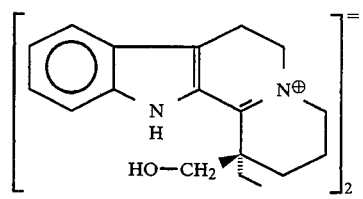

having an undesired optical active dissolved in a mother liquor; and
(c) separating the crystalline salt of the Formula (IV) from the mother liquor containing the salt of the Formula (V) and reducing the Formula (IV) salt to obtain the compound of the Formula (I).

2. The process defined in claim 1, wherein according to step (a) the compound of the Formula (II) is reacted with paraformaldehyde, in a protic or dipolar aprotic solvent or in a mixture of these solvents.

3. The process defined in claim 1, wherein according to step (c), the reduction of the optically active salt of the Formula (IV) is carried out using either a chemical reducing agent or catalytic hydrogenation.

4. A process for the preparation of an optically active compound of the Formula (I)

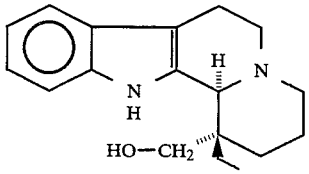

which comprises the steps of:
(a) asymmetrically transforming a compound of the Formula (II)

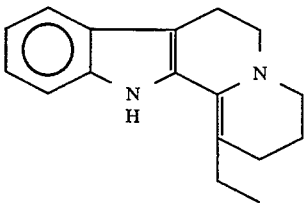

at a temperature near room temperature with about an equimolar amount of formaldehyde or with a polymerized form thereof, and with (−)-L-dibenzoyl-tartaric acid monohydrate, which is a resolving agent, wherein the compound of the Formula (II) is employed slightly in excess of the equivalent amount of the resolving compound to obtain a crystalline optically active salt of the Formula (IV)

(−)-L-dibenzoyl tartrate

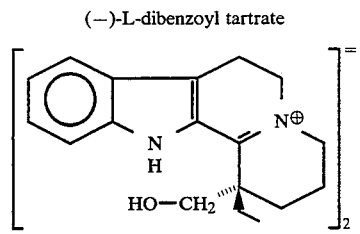

having a desired optical activity and an optically active salt of the Formula (V)

(−)-L-dibenzoyl tartrate

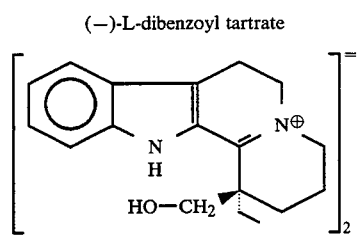

having an undesired optical activity dissolved in a mother liquor; and (b) separating the crystalline optically active salt of the Formula (IV) from the mother liquor containing the optically active salt of the Formula (V) and reducing the optically active Formula (IV) salt to obtain the compound of the Formula (I).

5. The process defined in claim 4, wherein according to step (a) the compound of the Formula (II) is reacted with paraformaldehyde and (−)-L-dibenzoyl tartaric acid monohydrate, in a protic or dipolar aprotic solvent or in a mixture of these solvents.

6. The process defined in claim 4, wherein according to step (b), the reduction of the optically active salt of the Formula (IV) is carried out using either a chemical reducing agent or catalytic hydrogenation.

7. A process for the preparation of an optically active compound of the Formula (I)

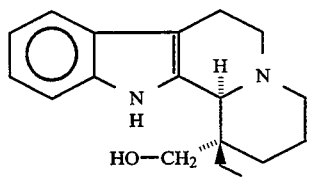

which comprises the steps of:

(a) asymmetrically transforming a racemic salt of the Formula ( IIa )

(−)-L-dibenzoyl tartrate

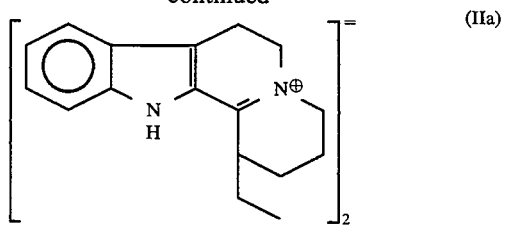

with about an equimolar amount of formaldehyde or with a polymerized form thereof, at a temperature near room temperature in the presence of a base to obtain a crystalline optically active salt of the Formula (IV)

(−)-L-dibenzoyl tartrate

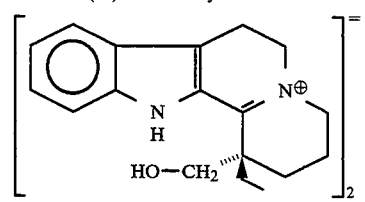

having a desired optical activity, and an optically active salt of the Formula (V)

(−)-L-dibenzoyl tartrate

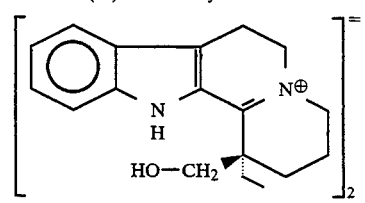

having an undesired optical activity dissolved in a mother liquor; and (b) separating the crystalline optically active salt of the Formula (IV) from the mother liquor containing the optically active salt of the Formula (V) and reducing the optically active Formula (IV) salt to obtain the compound of the Formula (I).

8. The process defined in claim 7, wherein according to step (a) the salt of the Formula (IIa) is asymmetrically transformed in a protic or dipolar aprotic solvent or in a mixture of these solvents using paraformaldehyde, and as the base triethylamine.

9. The process defined in claim 7, wherein according to step (a) the salt of the Formula (IIa) is asymmetrically transformed using as the base, the compound of the Formula (II)

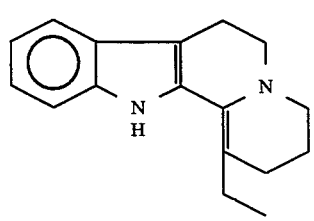

10. The process defined in claim 7, wherein according to step (b), the reduction of the optically active salt of the Formula (IV) is carried out using either a chemical reducing agent or catalytic hydrogenation.

* * * * *